United States Patent [19]

Binderup et al.

[11] Patent Number: 5,190,935
[45] Date of Patent: Mar. 2, 1993

[54] VITAMIN D ANALOGUES

[75] Inventors: Ernst T. Binderup, Tåstrup; Martin J. Calverley, Herlev, both of Denmark

[73] Assignee: Leo Pharmaceutical Products Ltd., Ballerup, Denmark

[21] Appl. No.: 773,950

[22] PCT Filed: Jul. 4, 1990

[86] PCT No.: PCT/DK90/00168
§ 371 Date: Nov. 19, 1991
§ 102(e) Date: Nov. 19, 1991

[87] PCT Pub. No.: WO91/00855
PCT Pub. Date: Jan. 24, 1991

[30] Foreign Application Priority Data

Jul. 10, 1989 [GB] United Kingdom ............... 8915770

[51] Int. Cl.⁵ ...................... A61K 31/59; C07J 175/00
[52] U.S. Cl. ..................................... 514/167; 552/653
[58] Field of Search ......................... 552/653; 514/167

[56] References Cited

U.S. PATENT DOCUMENTS 4,505,906 3/1985 De Luca et al. .

OTHER PUBLICATIONS

Calverley, M. J. Tetrahedron, 43 (20) pp. 4609–4619 (1987).
WO, A1, 85093939 (Sep. 12, 1985) see whole document.
Biochemical Pharmachology, vol. 37, No. 5, 1988 Lise Binderup et al: "Effects of a novel vitamin D analogue MC903 on cell proliferation and differentiation in vitro and on calcium metabolism in vivo", see page 889–895.

Primary Examiner—Howard T. Mars
Assistant Examiner—Kimberly J. Kestler
Attorney, Agent, or Firm—Cushman, Darby & Cushman

[57] ABSTRACT

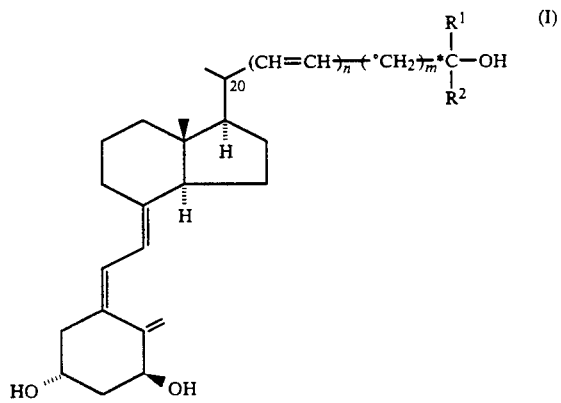

The present invention relates to compounds of formula (I), in which formula n is 2 or 3, m is 0 or an integer from 1–4; $R^1$ and $R^2$ (which may be the same or different) stand for hydrogen or $C_1$-$C_8$-hydrocarbyl, hydrocarbyl indicating the residue after removal of a hydrogen atom from a straight, branched or cyclic saturated or unsaturated hydrocarbon, or taken together with the carbon bearing the hydroxyl group (starred in formula (I)), $R^1$ and $R^2$ can form a saturated or unsaturated $C_3$-$C_8$ carboxylic ring; in addition, $R^1$ and/or $R^2$ and/or one of the m carbons designated by the "°" may be optionally substituted with one or more chlorine or fluorine atom(s); and finally one of the carbons designated "°" may optionally be substituted by one or two $C_1$-$C_2$ alkyl group(s); and derivatives of the compounds of formula (I) in which one or more hydroxy have been transformed into -O-acyl or O-glycosyl or phosphate ester groups; such masked groups being hydrolyzable in vivo. The present compounds find use in both the human and vertinary practice in the treatment and prophylaxis of autoimmune diseases (including diabetes mellitus), hypertension, acne, alopecia, skin ageing, imbalance in the immune system, inflammatory diseases such as rheumatoid arthritis and asthma as well as diseases characterized by abnormal cell differentiation and/or cell proliferation, such as e.g. psoriasis and cancer.

7 Claims, No Drawings

VITAMIN D ANALOGUES

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of a number of disease states including diabetes mellitus, hypertension, acne, alopecia, skin ageing, imbalance in the immune system, inflammatory diseases such as rheumatoid arthritis and asthma as well as diseases characterized by abnormal cell differentiation and/or cell proliferation such as e.g. psoriasis and cancer.

The compounds of the invention constitute a novel class of vitamin D analogues and are represented by the general formula I

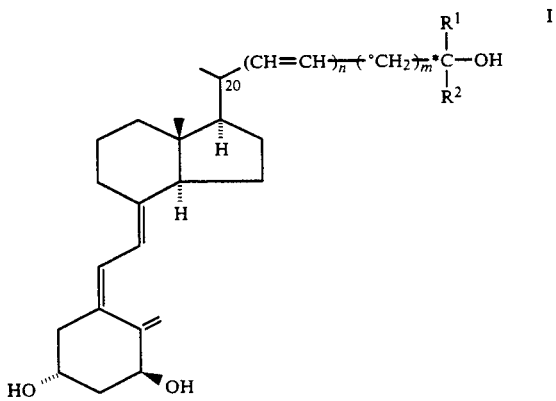

in which formula (and also throughout the remainder of this disclosure), n is 2 or 3, m is 0 or an integer from 1-4; $R^1$ and $R^2$ (which may be the same or different) stand for hydrogen or $C_1$-$C_8$-hydrocarbyl, or, taken together with the carbon bearing the hydroxyl group (starred in formula I), $R^1$ and $R^2$ can form a saturated or unsaturated $C_3$-$C_8$ carbocyclic ring. In addition, $R^1$ and/or $R^2$ and/or one of the m carbons designated by the "." may be optionally substituted with one or more chlorine or fluorine atom(s); and finally one of the carbons designated "*" may optionally be substituted by one or two $C_1$-$C_2$ alkyl group(s).

In the context of this invention, the expression hydrocarbyl radical indicates the residue after removal of a hydrogen atom from a straight, branched or cyclic saturated or unsaturated hydrocarbon.

Examples of $R^1$ and $R^2$ when taken separately include (apart from hydrogen), but are not limited to, methyl, trifluoromethyl, ethyl, vinyl, normal-, iso- and cyclopropyl, and 1-methylvinyl Examples of $R^1$ and $R^2$ when taken together include di-, tri-, tetra- and penta-methylene.

As can be seen from formula I, the compounds of the invention include diastereoisomeric forms (e.g. E or Z configuration of a side chain double bond; R or S configuration at C-20 and at the starred carbon atom depending on the meanings of $R^1$ and $R^2$). The invention covers all these diastereoisomers in pure form and also mixtures of diastereoisomers. It should be noted, however, that our investigations indicate a notable difference in activity between the stereoisomeric forms. In addition, derivatives of I in which one or more of the hydroxy groups are masked as groups which can be reconverted to hydroxy groups in vivo are also within the scope of the invention ("bioreversible derivatives or pro-drugs of I").

The term "bioreversible derivatives or prodrugs of I" includes but is not limited to. derivatives of the compounds of formula I in which one or more hydroxy groups have been transformed into -O-acyl or -O-glycosyl or phosphate ester groups, such masked groups being hydrolyzable in vivo.

Also within the scope of this disclosure is another type of prodrug of I in which the hydroxyl group at the starred carbon atom is replaced by a hydrogen atom. These compounds are relatively inactive in vitro, but are converted to active compounds of formula I by enzymatic hydroxylation after administration to the patient.

It has recently been shown that $1\alpha,25$-dihydroxyvitamin $D_3$ ($1,25(OH)_2D_3$) influences the effects and/or production of interleukins (Immunol. Lett. 17, 361–366 (1988)), indicating the potential use of this compound in the treatment of diseases characterized by a dysfunction of the immune system, e.g. autoimmune diseases, host versus graft reactions, and rejection of transplants or other conditions characterized by an abnormal interleukin-1 production, e.g. inflammatory diseases such as rheumatoid arthritis and asthma.

It has also been shown that $1,25(OH)_2D_3$ is able to stimulate the differentiation of cells and inhibit excessive cell proliferation (Abe, E. et al, Proc. Natl. Acad. Sci., U.S.A. 78, 4990–4994 (1981)), and it has been suggested that this compound might be useful in the treatment of diseases characterized by abnormal cell proliferation and/or cell differentiation such as leukemia, myelofibrosis and psoriasis.

Also, the use of $1,25(OH)_2D_3$, or its pro-drug $1\alpha$-OH-$D_3$, for the treatment of hypertension (Lind, L. et al, Acta Med. Scand. 222, 423–427 (1987)) and diabetes mellitus (Inomata, S. et al, Bone Mineral 1, 187–192 (1986)) has been suggested. Another indication for $1,25(OH)_2D_3$ is suggested by the recent observation of an association between hereditary vitamin D resistance and alopecia: treatment with $1,25(OH)_2D_3$ may promote hair growth (Lancet, Mar. 4, 1989, p. 478). Finally, the fact that topical application of $1,25(OH)_2D_3$ reduces the size of sebaceous glands in the ears of male Syrian hamsters suggests that this compound might be useful for the treatment of acne (Malloy, V. L. et al., the Tricontinental Meeting for Investigative Dermatology, Washington, 1989).

However, the therapeutic possibilities in such indications of $1,25(OH)_2D_3$ are severely limited by the well known potent effect of this hormone on calcium metabolism; elevated blood concentrations will rapidly give rise to hypercalcemia. Thus, this compound and its potent synthetic analogues are not completely satisfatory for use as drugs in the treatment of e.g. psoriasis, leukemia or immune diseases which may require continuous administration of the drug in relatively high doses.

A number of vitamin D analogues have recently been described which show some degree of selectivity in favour of the cell differentiation inducing/cell proliferation inhibiting activity as compared with the effect on calcium metabolism.

Thus, the vitamin $D_3$ analogue, MC 903, containing a 22,23-double bond, a 24-hydroxy group and in which the carbon atoms 25,26 and 27 are incorporated in a three membered ring, is a potent inducer of cell differentiation and inhibitor of cell proliferation which shows only moderate activity on calcium metabolism in vivo (Binderup, L. and Bramm, E., Biochemical Pharmacology 37, 889–895 (1988)). However, this selectivity is not paralleled by in vitro studies, which show that MC 903 binds equally well as 1,25(OH)$_2$D$_3$ to the intestinal vitamin D receptor. It may therefore be that the low in vivo activity on calcium metabolism of MC 903 is due to a rapid metabolism of the compound, thus limiting the potential of this compound for systemic use.

24-Homo-1,25-dihydroxyvitamin D$_3$ and 26-homo-1,25-dihydroxyvitamin D$_3$ (together with their 22,23-didehydroanalogues) (Ostrem, V. K.; Tanaka, Y.; Prahl, J.; DeLuca, H. F.; and Ikekawa, N.; Proc. Natl. Acad. Sci. USA 84, 2610–14 (1987)) have been claimed to have the same binding affinity as 1,25(OH)$_2$D$_3$ to both the rat and chicken intestinal receptor and the receptor in a human myeloid leukemia cell line (HL-60), and yet to be 10-fold more potent than 1,25(OH)$_2$D$_3$ in inducing differentiation of HL-60 cells in vitro. In vivo, these compounds are respectively "significantly less potent" and "more potent" than 1,25(OH)$_2$D$_3$ in calcium metabolism assessments.

26,27-Dimethyl-1α,25-dihydroxyvitamin D$_3$ has been synthesized, but the published information regarding its biological acitivities is contradictory. (Sai, H.; Takatsuto, S.; Hara, N.; and Ikekawa, N.; Chem. Pharm. Bull. 33, 878–881 (1985) and Ikekawa, N.; Eguchi, T.; Hara, N.; Takatsuto, S.; Honda, A.; Mori, Y.; and Otomo, S.; Chem. Pharm. Bull. 35, 4362–4365 (1987)). The closely related 26,27-diethyl-1α,25-dihydroxyvitamin D$_3$ is also reported by these authors; in this case as having "almost no vitamin D activity" (i.e. calcium metabolism effects) while being 10-fold more potent than 1,25(OH)$_2$D$_3$ in inducing cell differentiation.

The fact that there are only small structural differences between the above compounds indicates that the present state of knowledge does not allow prediction of the structure of vitamin D analogues which will show a favourable degree of selectivity, as reflected by a higher cell differentiating activity in vitro compared to the binding affinity for intestinal vitamin D receptor in vitro. Furthermore, the matter is complicated by the observation that receptor binding affinities in vitro are not always paralleled by in vivo studies, probably reflecting a pharmacokinetic difference between the compounds.

The compounds of the present invention are distinguished structurally from all vitamin D analogues which have been reported to have potent effects on cell differentiation/proliferation by the presence of a conjugated diene or triene moiety in the side chain.

Corresponding compounds which have a saturated side chain or an isolated double bond (22,23-didehydroderivatives) have been disclosed in international patent application No. PCT/DK89/00079, international filing date Apr. 7, 1989 and (for one pair of examples) in the Ostrem et al, reference discussed above, but none of these disclosures suggest methods for the incorporation of a conjugated polyene system into the side chain. Our synthetic studies have now opened up general routes to such polyene systems, and it has been surprisingly found that this type of functionality has an advantageous biological significance. Thus a particular compound of formula I, when compared to the corresponding compound in which all, or all but the 22,23-double bond, are saturated, is observed to show one or more of the following advantages:

(a) more potent effects on cell differentiation/proliferation;
(b) a greater selectivity in favour of the potent effects on cell differentiation/proliferation contra the effects on calcium metabolism;
(c) more potent effects on the production and action of interleukins;
(d) a greater selectivity in favour of the effects on interleukin production and action contra the effects on calcium metabolism.

An additional advantage conferred on the compounds I by the presence of the polyene moiety results from the more restricted conformational freedom of the side chain: the compounds I of the present invention are more readily obtained crystalline than the corresponding side chain saturated or partially saturated analogues.

The compounds of the invention are therefore especially suited for both local and systemic treatment and prophylaxis of human and veterinary disorders which are characterized by 1) abnormal cell proliferation and-/or cell differentiation, such as certain dermatological disorders including psoriasis and certain cancer forms, 2) an imbalance in the immune system, e.g in autoimmune diseases, including diabetes mellitus, host versus graft reaction, and rejection of transplants; and additionally for the treatment of inflammatory diseases, such as rheumatoid arthritis and asthma. Acne, alopecia, skin ageing (including photoageing), and hypertension are other conditions which may be treated with the compounds of the invention.

The present compounds may be used in combination with other pharmaceuticals. In the prevention of graft rejection and graft versus host reaction, a treatment with the present compounds may advantageously be combined with e.g. a cyclosporin treatment.

Compounds I can be prepared from the vitamin D-derived aldehyde lj [M. J. Calverley, Tetrahedron 43, 4609 (1987)]or lk, which may be obtained by triplet-sensitized photoisomerization of lj, optionally via the compounds 2 or 3 (Scheme 1). Schemes 2 to 4 illustrate reactions for the conversion of these key intermediates to compounds I in which n, m, R$^1$ and R$^2$ have various meanings.

The exemplified key intermediates of types 2 and 3 are listed in Table 1.

In the Schemes, the following abbreviations are used:

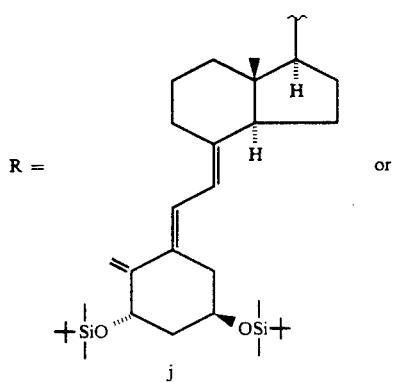

5

-continued

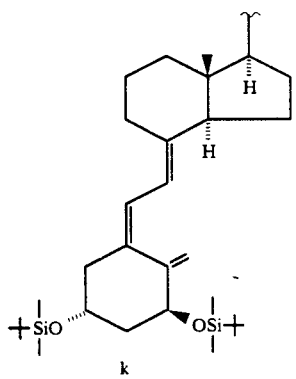
k

In the Notes to Schemes, appropriate aqueous work-up steps are implicit. The absolute configuration at C-20 can be either R or S. For explanation of the expression "side chain fragment", see following text.

-continued
Scheme 1

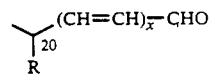

3a (20R)
3b (20S)  } (x = 1, 2 or 3)

Notes to Scheme 1

1j ⟶ 1k: hν - anthracene (toluene or CH₂Cl₂ containing trace Et₃N).

1 ⟶ 2: Ph₃⊕P—⊖CH—(CH=CH)ₓ₋₁—CO₂Me (heat in solvent e.g. toluene or CHCl₃).

2 ⟶ 3: (i) i-Bu₂AlH (THF); (ii) pyridinium dichromate (CH₂Cl₂).

3 (x = 1) ⟶ 2 (x = 3): Ph₃⊕P—⊖CH—(CH=CH)—CO₂Me (heat in solvent e.g. CHCl₃).

1 ⟶ 3 (x = 2)
3 (x = 1) ⟶ 3 (x = 3)  } : (i) (EtO₂P(O)—CH=CH—CH=N—cyclohexyl, LiN(Prⁱ)₂; (ii) hydrolysis during flash chromatography Scheme 2

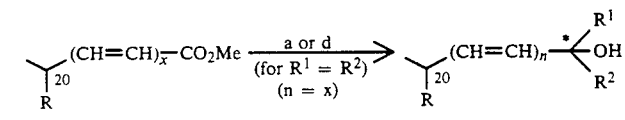

2a (20R)
2b (20S)  } (x = 1, 2 or 3)

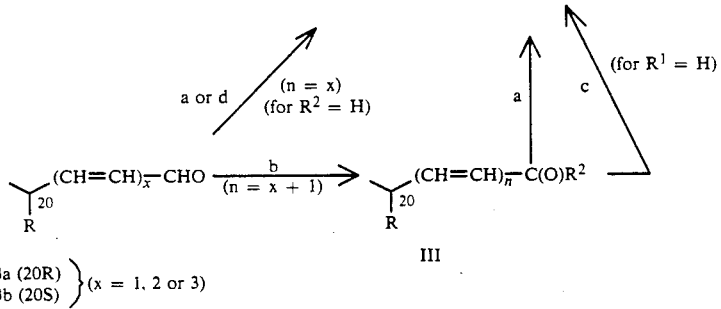

3a (20R)
3b (20S)  } (x = 1, 2 or 3)

Notes to Scheme 2
a. R¹MgBr (R¹MgI) or R¹Li (THF);
b. Metallated derivative or ylide (A') from side chain fragment A (anhydrous solvent or phase transfer conditions);
c. NaBH₄—CeCl₃ (THF-MeOH).
d. for R¹ = R² = H: i-Bu₂AlH (THF).

Scheme 3

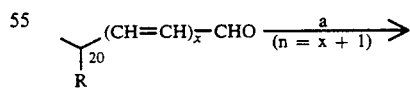

3a (20R)
3b (20S)  (x = 1, 2 or 3)

Scheme 1

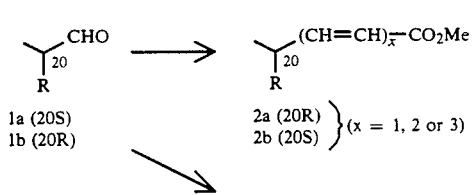

1a (20S)
1b (20R)

2a (20R)
2b (20S)  } (x = 1, 2 or 3)

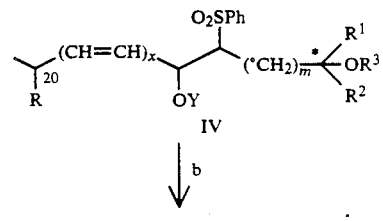

IV

↓ b

-continued
Scheme 3

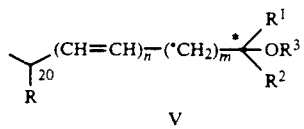

V

Notes to Scheme 3
a. (i) Metallated derivative (B') of side chain fragment B (THF); (ii) Optional derivatisation of the intermediate alkoxide (Y=M) or the isolated Y=H compound;
b. Reductive elimination mediated by e.g. Na—Hg [for Y=H, MeC(O)—, PhC(O)— or MeS(O$_2$)—]

Scheme 4

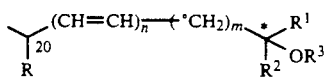

a  II (m = 0) or V   R = j
   II (m = 0) or V   R = k
b  I                 R$^3$ = H

Notes to Scheme 4
R$^3$ = H or alcohol protective group
a. anthracene - hv (toluene or CH$_2$Cl$_2$ containing trace Et$_3$N);
b. (i) n-Bu$_4$N$^+$F$^-$ (THF) or HF (MeCN—H$_2$O);
   (ii) any necessary reaction (sequence) for deprotecting OR$^3$ ⟶ OH.

A key step in some of the syntheses as described is the reaction with an intermediate (of type A' or B') which is obtained by treatment of a side chain fragment of type A or B respectively) either by conversion to an organometallic agent or to an ylide, as appropriate.

All these types of reactions are well known in the art of carbon-carbon bond formation in synthetic organic chemistry.

In general, the side chain fragments have the structure:

Z—C(O)—R$^2$   (type A)

Z—(.CH$_2$)$_m$—C(R$^1$)(R$^2$)—OR$^3$   (Type B)

with the following meanings (the following standard abbreviations are used throughout this disclosure: Et=ethyl; Hep=heptyl; Me=methyl; Ph=phenyl; Pr=propyl  THP=tetrahydro-4H-pyran-2-yl; THF=tetrahydrofuran; Ts  p-toluenesulphonyl; DMF=N,N-dimethylformamide):

For type A, Z=ph$_3$P$^{30}$—CH$_2$— or Z=Q$_2$P(O)—CH$_2$—, where Q=methoxy, ethoxy or phenyl, and the corresponding A' has Z=Ph$_3$P$^+$—CH— or Q$_2$P(O)—CHM— (M=metal e.g. Li).

For type B, Z=PhS(O$_2$)—CH$_2$—, and the corresponding B' has Z=PhS(O$_2$)—CHM—, where M=metal, e.g. Li.

R$^3$ is optionally hydrogen or an alcohol protective group such as tri(loweralkyl)silyl or THP. In the case where R$^3$=H in B, then R$^5$=M M=metal, e.g. XMg or Li) in the derived B'.

Fragments of type A, A' or B are known compounds or readily available as described for example in international patent application No. PCT/DK89/00079, international filing date Apr. 7, 1989, and British patent application No. 8914963.7, filing date Jun. 29, 1989. Some Examples are listed in Tables 2 and 3.

Some of these side chain fragements are converted (see Preparations and Examples) to the appropraite compounds I via the intermediates indicated in the Schemes. The intermediates are specified in Table 4 and the exemplified compounds I in Table 5.

Specific compounds I are also available by special reactions. For example, the compound 112 (Table 5) is obtained by isomerisation of MC 903 by treatment with trifluoroacetic anhydride, followed by saponification.

TABLE 1

Exemplified Key intermediates prepared from Compounds 1a or 1b (Scheme 1)

| Compound Number | Formula x | Configuration of side chain polyene* |
|---|---|---|
| 2aj | 1 | E |
| 2ak | 1 | E |
| 2aj | 2 | E,E |
| 2aj; isomer A | 3 | E,E,E |
| 2aj; isomer B | 3 | E,Z,E |
| 3aj | 1 | E |
| 2bj | 2 | E,E |
| 2ak | 3 | E,E,E |

*Reading from left to right.

TABLE 2

Some Specific Side Chain Fragments (Type A and A')
[Z—C(O)R$^2$]

| Compound Number+ | R$^2$ | Z |
|---|---|---|
| 4 | —CHMe$_2$ | Ph$_3$⊕PCH⊖ |
| 5 y = 1 |  —CH(CH$_2$)$_y$CH$_2$ | Ph$_3$⊕PCH⊖ |
| 5 y = 2 | | |
| 5 y = 3 | | |
| 5 y = 4 | | |
| 6 | —CCl—CH$_2$—CH$_2$ | Ph$_3$⊕PCH⊖ |
| 7 | 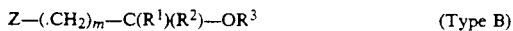 —CF—CH$_2$—CH$_2$ | (EtO)$_2$P(O)CH$_2$ |
| 8 | —CMe$_3$ | Ph$_3$⊕PCH⊖ |
| 9 | —CHEt$_2$ | Ph$_3$⊕PCH⊖ |
| 10 | —CH(n-Pr)$_2$ | Ph$_3$⊕PCH⊖ |

+As referred to in the Preparations

TABLE 3

Some Specific Side Chain Fragments (Type B)
[PhS(O$_2$)CH$_2$—(·CH$_2$)$_m$—C(R$^1$)(R$^2$)OR$^3$]

| Compound Number+ | m | Formula R$^1$ | R$^2$ | R$^3$ |
|---|---|---|---|---|
| 11 | 1 | Me | Me | H |
| 12 | 1 | Et | Et | H |
| 13 | 1 | —(CH$_2$)$_2$— | | THP |
| 14 | 2 | Et | Et | H |
| 15 | 3 | Me | Me | H |
| 16 | 4 | Me | Me | H |
| 17++ | 1 (CH(Me)) | Me | Me | H |
| 18** | 1 (CH(Me)) | Me | Me | H |

+As referred to in the Preparations
++S-Form
**R-Form

Unsubstituted CH$_2$ unless otherwise indicated by specifying an alternative meaning of "(·CH$_2$)".

TABLE 4

Compounds of Schemes 2-4 which are Intermediates in the Preparation of Compounds I of Scheme 4

| Compound Number (R = j or k) | Type | Scheme | n | m | $R^1$ | $R^2$ | $R^3$ | Configuration of the side chain polyene* | Configuration at C-20 |
|---|---|---|---|---|---|---|---|---|---|
| 101j | III | 2 | 2 | — | — | —CHCH$_2$CH$_2$ | — | E,E | R |
| 102j | II | 2 | 2 | — | H | —CHCH$_2$CH$_2$ | — | E,E | R |
| 103j | II | 2 | | | | | | | |
| 102k | II | 4 | 2 | — | H | —CHCH$_2$CH$_2$ | — | E,E | R |
| 103k | II | 4 | | | | | | | |
| 104j | II | 2 | 2 | — | Me | Me | — | E,E | R |
| 104k | II | 4 | 2 | — | Me | Me | H | E,E | R |
| 105j | II | 2 | 2 | — | Et | Et | — | E,E | R |
| 105k | II | 4 | 2 | — | Et | Et | H | E,E | R |
| 106j | II | 2 | 3 | — | Me | Me | — | E,E,E | R |
| 107j | V | 3 | 2 | 1 | Me | Me | H | E,E | R |
| 107k | II | 4 | 2 | 1 | Me | Me | H | E,E | R |
| 113j | II | 2 | 2 | — | Me | Me | — | E,E | S |
| 113k | II | 4 | 2 | — | Me | Me | H | E,E | S |
| 114j | II | 2 | 2 | — | Et | Et | — | E,E | S |
| 114k | II | 4 | 2 | — | Et | Et | H | E,E | S |
| 117j | II | 2 | 2 | — | H | H | — | E,E | S |
| 117k | II | 4 | 2 | — | H | H | H | E,E | S |
| 119j | II | 2 | 2 | — | Pr | Pr | — | E,E | R |
| 119k | II | 4 | 2 | — | Pr | Pr | H | E,E | R |
| 121j | II | 2 | 2 | — | H | H | — | E,E | R |
| 121k | II | 4 | 2 | — | H | H | H | E,E | R |
| 123k | II | 2 | 1 | — | H | H | — | E | R |
| 124k | II | 2 | 3 | — | Me | Me | — | E,E,E | R |
| 126k | II | 2 | 3 | — | Et | Et | — | E,E,E | R |
| 128k | II | 2 | 3 | — | H | H | — | E,E,E | R |

Note as for Table 3
*Reading from left to right
NB Where identical descriptions for two numbered compounds are given (e.g. 102j and 103j) the compounds are distinguished only in their configuration at the starred carbon atom. These configurations give rise to two series of compounds, referred to as "isomer A" and "isomer B" in the Preparations and Examples.

TABLE 5

Exemplified Compounds I

| Compound Number | m | n | $R^1$ | $R^2$ | Configuration of side chain polyene* | Configuration at C-20 |
|---|---|---|---|---|---|---|
| 108 | 0 | 2 | H | —CHCH$_2$CH$_2$ | E,E | R |
| 109 | | | | | | |
| 110 | 0 | 2 | Me | Me | E,E | R |
| 111 | 0 | 2 | Et | Et | E,E | R |
| 112 | 1 | 2 | H | H | E,E | R |
| 115 | 0 | 2 | Me | Me | E,E | S |
| 116 | 0 | 2 | Et | Et | E,E | S |
| 118 | 0 | 2 | H | H | E,E | S |
| 120 | 0 | 2 | Pr | Pr | E,E | R |
| 122 | 0 | 2 | H | H | E,E | R |
| 125 | 0 | 3 | Me | Me | E,E,E | R |
| 127 | 0 | 3 | Et | Et | E,E,E | R |
| 129 | 0 | 3 | H | H | E,E,E | R |
| 130 | 1 | 2 | H | H | E,E | S |
| 131 | 0 | 2 | H | —CHCH$_2$CH$_2$ | E,E | S |
| 132 | | | | | | |
| 133 | 1 | 2 | Me | Me | E,E | R |
| 134 | 1 | 2 | Me | Me | E,E | S |
| 135 | 1 | 2 | Et | Et | E,E | S |
| 136 | 1 | 2 | Et | Et | E,E | R |
| 137–38 | 1(CH(Me)) | 2 | Me | Me | E,E | R |
| 139–40 | 1(CH(Me)) | 2 | Me | Me | E,E | S |

Notes as for Table 4

Parallel reactions can be used to convert other side chain fragments to the corresponding compounds I.

In cases where $R^1 \neq R^2$ in compounds II or V, the isomers can be separated and the configuration at the starred carbon atom can be inverted or equilibrated at this stage by application of standard reactions.

The synthesis of the prodrugs of compounds I which lack the side chain hydroxyl (at the starred carbon atom) may follow the route of Scheme 3, using the appropriate side chain fragment of structure $Z-(^\circ CH_2 )_m-CH(R^1)(R^2)$.

The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the disease state which is to be treated, the route of administration and the mammal under treatment. The compounds of the invention can be administered by the parenteral, intra-articular, enteral or topical routes. They are well absorbed when given enterally and this is the preferred form of administration in the treatment of systemic disorders.

Conveniently, the active ingredient comprises from 0.1-100 μg/g for topical formulations and 0.05-100 μg/g for oral and parenteral formulations.

By the term "dosage unit" is meant a unitary, i.e. a single dose which is capable of being administered to a patient as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including transdermal, subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100 μ.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$-$C_6$-alkyl hydrocarbons or halogenated $C_1$-$C_6$-alkyl hydrocarbons or mixtures thereof; chlorinated and flourinated $C_1$-$C_6$-alkyl hydrocarbons are especially preferred. Generally, the propellant constitutes 45 to 99.9% w/w of the formulation whilst the active ingredient constitutes 1 ppm to 0.1% w/w, of the formulation.

In addition to the aforementioned ingredients, the formulations of this invention may include one or more additional auxiliary ingredients such as diluents, buffers, flavouring agents, binders, surface active agents, thickeners, lubricants, preservatives, e.g. methyl hydroxybenzoate (including anti-oxidants), emulsifying agents and the like.

The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.01–100 μg, preferably from 0.025–50 μg, of a compound of formula I are administered. In the topical treatment of dermatological disorders, ointments, creams or lotions containing from 3.1–100 μg/g, and preferably from 0.5–10 μg/g, of a compound of formula I are administered. The oral compositions are formulated, preferably as tablets, capsules, or drops, containing from 0.01–100 μg, preferably from 0.025–50 μg, of a compound of formula I, per dosage unit.

The invention will now be further described in the following non-limiting Preparations and Examples:

PREPARATIONS AND EXAMPLES

General

The compounds referred to in the Preparations and Examples are to be identified by number or letter with the corresponding formulae in the Schemes and/or Tables. Ultra-violet spectra (λ) were measured for solutions in 96% ethanol. For nuclear magnetic resonance spectra chemical shift values (δ) are quoted in p.p.m. for deuteriochloroform solutions relative to internal tetramethylsilane (δ=0) or chloroform (δ=7.25). The value for a multiplet, either defined (doublet (d), triplet (t), quartet (q)) or not (m) at the approximate mid point is given unless a range is quoted (s=singlet, b TM broad) Coupling constants (J) are given in Hertz, and are sometimes approximated to the nearest unit.

Ether is diethyl ether, and was dried over sodium. THF was dried over sodium-benzophenone. Petroleum ether refers to the pentane fraction. Brine is saturated sodium chloride solution. Organic solutions were dried over dried magnesium sulphate and concentrated on a rotary evaporator at water aspirator pressure.

Preparation 1 Compound lak

A mixture of anthracene (0.10 g), triethylamine (20 mg), and the compound laj (0.20 g) in toluene (15 ml), stirred under an atmosphere of nitrogen in a Pyrex flask immersed in a water bath at 20° C., was illuminated with radiation from a high pressure Hg lamp (type: Hanau TQ 718Z2) for 30 minutes. The reaction mixture was filtered and concentrated in vacuo to give a residue. This was purified by chromatography (30 g silica gel, using 5% ether in petroleum ether as eluant) to give lak; δ(300 MHz) 0.05 (12H, bs), 0.56 (3H, s), 0.86 (18H, s), 1.12 (3H, d, J 7), 1.15–2.05 (13H, m), 2.20 (1H, dd), 2.35 (1H, m), 2.43 (1H, m), 2.81 (1H, bd), 4.18 (1H, m), 4.36 (1H, m), 4.84 (1H, m), 5.16 (1H, m), 6.01 (1H, d, J 11), 6.21 (1H, d, J 11) and 9.57 (1H, d, J 3).

Preparation 2: Compound 2aj (x=1)

A stirred solution of laj (3.9 g), and methoxycarbonylmethylene-triphenylphosphorane (4.6 g) in toluene (40 ml) was heated under reflux for 3 hours. The reaction mixture was cooled, filtered, and concentrated in vacuo. Purification of the residue by chromatography (200 g silica gel; 5% ether in petroleum ether as eluant) followed by recrystallization from ether-methanol gave 2aj (x=1), as needles, m.p. 129°–130° C., δ(300 MHz) 0.05 (12H, bs), 0.56 (3H, s), 0.86 (9H, s), 0.89 (9H, s), 1.09 (3H, d, J 6.6), 1.1–2.1 (13H, m), 2.28 (2H, m), 2.54 (1H, dd), 2.87 (1H; dd), 3.71 (13H, s), 4.21 (1H, m), 4.52 (1H, m), 4.94 (1H, bs), 4.98 (1H, bs), 5.75 (1H, d, J 15.5), 5.81 (1H, d, J 11.5), 6.43 (1H, d, J 11.5), 6.84 (1H, dd, J 15.5 and 9 0).

Preparation 3: Compound 2ak (x=1)

The compound was prepared using the procedure of Preparation 2, but using lak as starting material instead of laj. The product was not obtained crystalline after this chromatographic purification, δ (300 MHz) in agreement with assigned structure.

Procedure 1

Reduction of Compound 2 or 3 to the Corresponding Compound II (Scheme 2)

To a stirred solution of 2 or 3 (5 mmol) in dry THF (25 ml) at −70° C. under $N_2$ was added diisobutylaluminium hydride (1M solution in hexanes, 15 ml for compound 2; 8 ml for compound 3) dropwise. After stirring for 30 minutes, methanol (3 ml) was added dropwise, and the reaction mixture was allowed to warm up to room temperature. EtOAc and water were added, and after stirring for an additional 30 minutes, the organic phase was separated, washed with brine, dried and concentrated to give II, which was optionally purified by chromatography and/or recrystallisation.

Preparation 4: 1

1(S),3(R)-bis-tert-butyldimethylsilyloxy-20(R)-(3'-hydroxyprop-1'(E)-enyl)-9,10-secopregna-5(E),7(E),10(19)-triene The compound was prepared using Procedure 1 in which the starting material was compound 2aj (x=1). The crude product was of sufficient purity for use as starting material in Preparation 5. An analytical sample was obtained by recrystallisation from ether-MeOH; m.p. 118°–120° C.; δ(300 MHz) 0.05 (12H, bs), 0.55 (3H, s), 0.86 (9H, s), 0.89 (9H, s), 1.04 (3H, d, J 6), 1.10–2.20 (15H, m), 2.29 (1H, d), 2.54 (1H, dd), 2.87 (1H, m), 4.06 (2H, m), 4.21 (1H, m), 4.52 (1H, m), 4.93 (1H, bs), 4.g8 (1H, bs), 5.56 (2H, ml, 5.82 (1H, d, J 11.5), 6.44 (1H, d, J 11.5).

Preparation 5: Compound 3aj (x =1)

Pyridinium dichromate (0.5 g) was added at room temperature to a stirred solution of the compound from Preparation 4 (0.53 g) in dichloromethane (10 ml). After stirring for 3 hours the mixture was diluted with ether and filtered. The filtrate was concentrated in vacuo and purified by chromatography (silica gel, hexane:ether 4:1 as eluant) to give 3aj (x=1) which crystallized on treatment with methanol. M.p.: 101°–103° C.; δ(300 MHz) 0.06 (12H, m), 0.59 (3H, s), 0.86 (9H,s), 0.89 (9H, s), 1.15 (3H, d, J 6.6), 1.20–2.10 (13H, m), 2.30 (1H, bd), 2.42 (1H, m), 2.55 (1H, dd), 2.89 (1H, m), 4.21 (1H, m), 4.53 (1H, m), 4.94 (1H, m), 4.98 (1H, m), 5.82 (1H, d, J 11.4), 6.06 (1H, dd, J 15.6 and 7.8), 6.44 (1H, d, J 11.4), 6.71 (1H, dd, J 15.6 and 8.8), 9.48 (1H, d, J 7.8).

Preparation 6: Compound 2aj (x=2)

A mixture of 1aj (4.56 g), 3-(methoxycarbonyl)-2-propenyl-1-idene-triphenylphosphorane (3.03 g) and alcohol-free chloroform (12 ml) was heated at 62° C. with stirring under $N_2$ while part of the chloroform was evaporated in vacuo. The mixture was kept at 62° C. overnight, cooled and partitioned between ether and water. The organic layer was dried and evaporated in vacuo. The resulting oil was purified by chromatography (silica gel, hexane-ether 97:3 as eluant) to give an oil which crystallized from ether/methanol. M.p.: 99°-101° C.; $\lambda_{max}$=268 nm ($\epsilon$=52372); δ(300 MHz) 0.05 (12H, m), 0.56 (3H, s), 0.85 (9H, s), 0.89 (9H, s), 1.07 (3H, d, J 6.69), 1.17-2.10 (13H, m), 2.25 (2H, m), 2.55 (1H, dd), 2.87 (1H, m), 3.73 (3H, s), 4.21 (1H, m), 4.52 (1H, m), 4.94 (1H, m), 4.98 (1H, m), 5.78 (1H, d, J 15.3), 5.81 (1H, d, J 11.4), 6.05 (2H, m), 6.44 (1H, d, J 11.4), 7.24 (1H, dd).

Preparation 7: Compound 2aj (x=3) Isomers A and B

A mixture of 3aj (x=1) (1 g), 3-(methoxycarbonyl) TM 2-propenyl-1-idene-triphenylphosphorane (1.26 g) and alcohol-free chloroform (3 ml) was heated with stirring at 62° C. while part of the chloroform was evaporated in vacuo. After 2 hours at 62° C. the mixture was cooled and partitioned between ether and water. The organic layer was dried, concentrated and purified by chromatography (silica gel, hexane-ether 9 1 as eluant). The first eluted title compound was isomer B; δ(300 MHz) 0.06 (12H, m), 0.58 (3H, s), 0.86 (9H, s), 0.89 (9H, s), 1.08 (3H, d, J 6,6) 1.17-2.35 (15H, m), 2.58 (1H, dd), 2.88 (1H, m), 3.75 (3H, s), 4.21 (1H, m), 4.53 (1H, m), 4,94 (1H, m), 4.98 (1H, m), 5.82 (3H, m), 5.98 (1H, t, J 11.2), 6.26 (1H, t, J 11.2), 6.45 (1H, d, J 11.3), 6.57 (1H, dd), 7.75 (1H, m). The second eluted title compound was isomer A; δ (300 MHz) 0.05 (12H, m), 0.56 (3H, s), 0.86 (9H, s), 0.89 (9H, s), 1.07 (3H, d, J 6,6), 1.15-2.35 (15H, m), 2.55 (1H, dd), 2.87 (1H, m), 3.73 (3H, s), 4.21 (1H, m), 4.52 (1H, m), 4.93 (1H, m), 4.98 (1H, m), 5.81 (3H, m), 6.07 (1H, dd), 6.20 (1H, dd), 6.48 (2H, m), 7.29 (1H, dd).

Procedure 2

Reaction of Compound 3 with side chain fragment A'(Z=Ph$_3$P$^\oplus$—Ch$^\ominus$) to give Compound III (Scheme 2)

A stirred mixture of 3 and a molar excess of A' in toluene (5-10 ml per gram 1) was heated under reflux under an $N_2$ atmosphere until a reasonable or complete conversion of 3 was obtained (4 to 16 hours). After cooling, the mixture was filtered, and the filtrate concentrated and purified by chromatography (5-20% ether in hexane or petroleum ether for the examples of Table 2) to give III.

Preparation 8: Compound 101j

Using the method of Procedure 2, a mixture of 3aj (x=1) (0.6 g) and cyclopropylcarbonylmethylenetriphenylphosphorane (5a) (0.86 g) and toluene (4 ml) was stirred at 110° C. for 4 hours. After cooling to room temperature and filtration, the filtrate was concentrated in vacuo and purified by chromatography (silica gel, hexane-ether 85:5 as eluant) to give 101j as an oil which crystallized from methanol. M.p.: 106°-108° C.; $\lambda_{max}$279 2 nm (δ=50220); δ(300 MHz) 0.05 (12H, m), 0.56 (3H, s), 0.86 (9H, s), 0.89 (9H, s), 0.80-0.95 (2H, m), 1.00-1.15 (2H, m), 1.08 (3H, d, J 6.5), 1.17-2.35 (16H, m), 2.55 (1H, dd), 2.88 (1H, m), 4.21 (1H, m), 4.53 (1H, m), 4.93 (1H, m), 4.98 (1H, m), 5.81 (1H, d, J 11.4), 6.12 (3H, m), 6.44 (1H, d, J 11.4), 7.18 (1H, dd).

Procedure 3

Reduction of Compound III to Compound II ($R^1$=H) (Scheme 2)

Sodium borohydride (0.29 g) was added to an ice-cooled, stirred solution of III (2.5 g) in tetrahydrofuran (8 ml) and 0.4M CeCl$_3$.7H$_2$O in ethanol (11.5 ml). Methanol (6 ml) was added over 10 minutes and after stirring for a further 20 minutes the mixture was partitioned between ethyl acetate and water. The organic layer was washed with water, dried and concentrated in vacuo. The residue was purified by chromatography to give the compound II.

Preparation 9: Compounds 102j and 103j

Using the method of Procedure 3 (101j as starting material), two isomers were isolated by chromatography (3% acetone in toluene as eluant). First eluted isomer was 102j; δ(300 MHz) 0.05 (12H, m), 0.20-0.40 (2H, m), 0.56 (3H, s), 0.45-0.60 (2H, m), 0.86 (9H, s), 0.89 (9H, s), 1.05 (3H, d, J 6.6), 0.70-2.35 (17H, m), 2.56 (1H, dd), 2.87 (1H, m), 3.48 (1H, t), 4.21 (1H, m), 4.53 (1H, m), 4.93 (1H, m), 4.98 (1H, m), 5.56 (1H, dd, J 15 and 8.6), 5.65 (1H, dd, J 15 and 6.6), 5.81 (1H, d, J 11.4), 5.97 (1H, dd, J 15 and 10.4), 6.17 (1H, dd, J 15 and 10.4), 6.45 (1H, d, J 11.4). Second eluted isomer was 103j; δ(300 MHz) 0.05 (12H, m), 0.20-0.40 (2H, m), 0.56 (3H, s), 0.44-0.65 (2H, m), 0.86 (9H, s), 0.89 (9H, s m), 2.56 (1H, dd), 2.87 (1H, m), 3.49 (1H, t), 4.21 (1H, m), 4.53 (1H, m), 4.94 (1H, m), 4.98 (1H, m), 5.57 (1H, dd, J 15 and 8.6), 5.66 (1H, dd, J 15 and 6.4), 5.81 (1H, d, J 11.4), 5.97 (1H, dd, J 15 and 10.4), 6.19 (1H, dd, J 15 and 10.4), 6.45 (1H, d, J 11.4).

Procedure 4

Reaction of Compound 2 or 3 with $R^1Li$ to give Compound II (Scheme 2)

Alkyl-lithium (in ether, 3 molar equivalents for compound 2; 1.5 molar equivalent for compound 3) was added dropwise at −45° C. to a stirred solution of compound 2 or 3 (0.16 g) in dry THF (5 ml). After a further 50 minutes at −45° C. the mixture was partitioned between ether and water. The organic layer was washed with brine, dried, and concentrated. The residue was purified by chromatography (silica gel) to give II.

Preparation 10 Compound 104j

The compound was prepared using procedure 4 in which the alkyl-lithium was methyl-lithium (1.5M) and the starting material was 2aj (x=2). (Eluant: hexane-ether; 85:15). 104j δ(300 MHz) 0.06 (12H, m), 0.56 (3H, s), 0.87 (9H, s), 0.90 (9H, s), 1.05 (3H, d, J 6.6), 1.33 (6H, s), 1.15-2.35 (16H, m), 2.56 (1H, dd), 2.87 (1H, m), 4.21 (1H, m), 4.53 (1H, m), 4.94 (1H, m), 4.98 (1H, m), 5.56 (1H, dd, J 15 and 8.6), 5.70 (1H, d, J 15.3), 5.81 (1H, d, J 11.4), 5.95 (1H, dd, J 15 and 10.3), 6.15 (1H, dd, J 15 and 10.3), 6.45 (1H, d, J 11.4).

Preparation 11 Compound 105j

The compound was prepared using procedure 4 in which the alkyl-lithium was ethyl-lithium (1.5M) and the starting material was 2aj (x=2). (Eluant: hexane-ether; 85:15). The compound crystallized from MeOH;

m.p.: 84°–85° C., $\lambda_{max}$232 nm ($\epsilon$=37350) and 269.5 nm ($\epsilon$=26900); 105j $\delta$(300 MHz) 0.06 (12H, m), 0.56 (3H, s), 0.86 (9H, s), 0.89 (9H, s), 0.86 (6H, t), 1.05 (3H, d, J 6.6), 1.20–2.20 (19H, m), 2.30 (1H, bd), 2.56 (1H, dd), 2.87 (1H, m), 4.21 (1H, m), 4.53 (1H, m), 4.94 (1H, m), 4.98 (1H, m), 5.52 (1H, dd, J 15.3), 5.54 (1H, dd, J 15 and 8.6), 5.82 (1H, d, J 11.4), 5.97 (1H, dd, J 15 and 10.3), 6.15 (1H, dd, J 15 and 10.3), 6.45 (1H, d, J 11.4).

Preparation 12 Compound 106j

The compound was prepared using procedure 4 in which the alkyl-lithium was methyl-lithium (1.5M) and the starting material was 2aj (x=3) isomer A. (Eluant: hexane-ether; 85:15). 106j $\delta$ (300 MHz) in agreement with structure.

Procedure 5

Preparation of Compounds V from Aldehyde (3) and Side Chain Fragment B (Scheme 3)

A solution of lithium di-iso-propylamide (0.4M in THF-hexanes, 3:1) was added dropwise via a syringe (10 minutes) to a solution of the side chain fragment B in dry THF (8 ml), stirred at −25° C. under nitrogen. The resulting yellow solution was then cooled to −40° C., and a solution of the aldehyde (3) (2 mmol) in dry THF (8 ml) was added dropwise (5 minutes). After stirring for 30 minutes, benzoyl chloride (0.6 ml) was added dropwise, and the mixture was allowed to warm to 0° C. for a further 30 minutes. The reaction mixture was treated with ether (10 ml) and water (1 ml) and partitioned between ethyl acetate (100 ml) and water (50 ml). The organic layer was washed with brine, dried, and concentrated in vacuo to give a crude oil containing compound IV (Y =PhC(O)) as a mixture of diastereoisomers. This was dissolved in ethyl acetate (5 ml) and diluted with methanol (50 ml, saturated with and containing suspended disodium hydrogen phosphate). To the ice-cooled mixture was added sodium amalgam (ca. 5% Na, 15 g), and the reaction mixture was stirred at 5° C. under nitrogen for 15 hours. The mixture was then partitioned between ethyl acetate (200 ml) and water (200 ml) (decanting from the mercury), and the organic layer was washed with brine, dried and concentrated in vacuo. Purification of the residue by chromatography gave V.

Preparation 13 Compound 107j

This compound was prepared using Procedure 5 [aldehyde 3aj (x=1) a starting material] in which the side chain fragment B was compound 11 (0.55 g) and 12 ml of the lithium di-iso-propylamide solution was used. The intermediate IV has $R^3$ =OH. The chromatography was performed on 150 g silica gel using 10% ethyl acetate in petroleum ether as eluant. 107j; $\delta$ 0.05 (6H, bs), 0.56 (3H, s), 0.86 (9H, s), 0.89 (9H, s), 1.04 (3H, d, J 6), 1.1–2.70 (31H, m), 2.86 (1H, bd), 4.21 (1H, bs), 4.52 (1H, m), 4.94 (1H, bs), 4.98 (1H, bs), 5.45–5.65 (2H, m), 5.82 (1H, d, J 11), 5.9–6.20 (2H, m), 6.44 (1H, d, J 11).

Procedure 6

Preparation of Compound II or V (R=k) from the Corresponding Compound (R=j) (Scheme 4)

A mixture of anthracene (0.10 g), triethylamine (20 mg), and the compound II or V (R=j) (0.20 g) in dichloromethane (15 ml), stirred under an atmosphere of nitrogen in a Pyrex flask immersed in a water bath at 20° C., was illuminated with radiation from a high pressure Hg lamp (type: Hanau TQ 718Z2) for 30 minutes. The reaction mixture was filtered and concentrated in vacuo to give a residue. This was purified by chromatography (30 g silica gel) to give II or V (R=k).

Preparation 14 Compound 102k

The compound was prepared using Procedure 6 in which starting material II was compound 102j. (Eluant: toluene-acetone, 97:3) 102k; $\delta$ (300 MHz) 0.05 (12H, s), 0.18–0.40 (2H, m), 0.54 (3H, s), 0.45–0.65 (2H, m), 0.87 (18H, s), 1.04 (3H, d, J 7), 0.80–2.35 (16H, m), 2.44 (1H, dd), 2.80 (1H, bd), 2.58 (1H, m), 2.81 (1H, m), 3.49 (1H, t), 4.18 (1H, m), 4.36 (1H, m), 4.85 (1H, d, J 2), 5.17 (1H, m), 5.61 (2H, m), 5.97 (2H, m), 6.18 (2H, m).

Preparation 15 Compound 103k

The compound was prepared using Procedure 6 in which starting material II was compound 103j. (Eluant: toluene-acetone, 97:3) 103k; $\delta$ (300 MHz) 0.05 (12H, s), 0.18–0.40 (2H, m), 0.54 (3H, s), 0.45–0.65 (2H, m), 0.87 (18H, s), 1.04 (3H, d, J 7), 0.80–2.35 (16H, m), 2.44 (1H, dd), 2.80 (1H, bd), 2.81 (1H, m), 3.48 (1H, t), 4.16 (1H, m), 4.36 (1H, m), 4.85 (1H, m), 5.17 (1H, m), 5.61 (2H, m), 5.97 (2H, m), 6.18 (2H, m).

Preparation 16 Compound 104k

The compound was prepared using Procedure 6 in which starting material II was compound 104j. (Eluant: 25% ether in petroleum ether) 104k; $\delta$ (300 MHz) 0.05 (12H, bs), 0.54 (3H, s), 0.88 (18H, s), 1.04 (3H, d, J 7), 1.32 (6H, s), 1.15–2.35 (16H, m, including 1.19 (6H, s)), 2.20 (1H, dd, J 13 and 7), 2.43 (1H, dd), 2.81 (1H, m) 4.18 (1H, m), 4.36 (1H, m), 4.86 (1H, bd), 5.17 (1H, dd), 5.55 (1H, dd), 5.69 (1H, d, J 15), 5.96 (2H, m), 6.22 (1H, d, J 11), Preparation 17 Compound 105k The compound was prepared using Procedure 6 in which starting material II was compound 105j. (Eluant: 25% ether in petroleum ether) 105k; $\delta$ (300 MHz) 0.05 (12H, m), 0.54 (3H, s), 0.85 (6H, t), 0.87 (18H, s), 1.04 (3H, d), 1.15–2.15 (19H, m), 2.20 (1H, dd), 2.43 (1H, dd), 2.82 (1H, bd), 4.18 (1H, m), 4.36 (1H, m), 4.85 (1H, m), 5.16 (1H, m), 5.51 (1H, d, J 15.3), 5.53 (1H, dd, J 15.0 and 8.7), 5.96 (1H, dd, J 15.0 and 13.0), 6.00 (1H, d), 6.14 (1H, dd, J 15.3 and 10.3), 6.22 (1H, d).

Preparation 18 Compound 2bj (x=2)

Using the method of Preparation 6 and by starting from 1bj (see British patent application No. 8914963.7) instead of 1aj, compound 2bj was obtained as an oil which crystallized from ether/methanol. M.p.: 108°–110° C.; $\delta_{max}$=268 nm ($\epsilon$=50887); $\delta$ (300 MHz) 0.05 (12H, bs), 0.48 (3H, s), 0.86 (9H, s), 0.88 (9H, s), 0.97 (3H, d), 1.05–2.05 (13H, m), 2.20 (1H, m), 2.30 (1H, bd), 2.53 (1H, dd), 2.84 (1H, bd), 3.72 (3H, s), 4.21 (1H, m), 4.51 (1H, m), 4.92 (1H, bs), 4.97 (1H, bs), 5.77 (1H, dd), 5.79 (1H, d), 5.95–6.15 (2H, m), 6.43 (1H, d), 7.25 1H., dd).

Preparation 19 Compound 113j

The compound was prepared using Procedure 4 in which the alkyl-lithium was methyl-lithium, and the starting material was 2bj (x=2). 113j crystallized from MeOH; $\delta_{max}$232 nm ($\epsilon$35228) and 269 nm ($\epsilon$25416); $\delta$ (300 MHz) 0.05 (12H, m), 0.49 (3H, s), 0.85 (9H, s), 0.89 (9H, s), 0.94 (3H, d, J 6.6), 1.34 (6H, s), 1.00–2.15 (15H, m), 2.30 (1H, bd), 2.55 (1H, dd), 2.85 (1H, bd), 4.21 (1H, m), 4.52 (1H, m), 4.93 (1H, m), 4.98 (1H, m), 5.55 (1H, dd), 5.68 (1H, d), 5.81 (1H, d, J 11.4), 5.91 (1H, dd), 6.15 (1H, dd), 6.45 (1H, d, J 11.4).

Preparation 20 Compound 113k

The compound was prepared using Procedure 6 in which starting material II was compound 113j. (Eluant: hexane-ether 80:20) 113k; δ (300 MHz) 0.05 (12H, m), 0.48 (3H, s), 0.85 (9H, s), 0.86 (9H, s), 0.93 (3H, d, J 6.6). 1.33 (6H, s), 1.00-2.15 (15H, m), 2.20 (1H, dd), 2.43 (1H, dd), 2.80 (1H, bd), 4.18 (1H, m), 4.35 (1H, m), 4.85 (1H, m), 5.17 (1H, m), 5.54 (1H, dd), 5.68 (1H, d), 5.91 (1H, dd), 5.99 (1H, d, J 11.3). 6.15 (1H, dd), 6.22 (1H, d, J 11.3).

Preparation 21 Compound 114j

The compound was prepared by following the procedure described in Preparation 19 and by using ethyl-lithium instead of methyl-lithium. (Eluant: hexane-ether 80:20) 14j; δ (300 MHz) 0.05 (12H, m), 0.50 (3H, s), 0.85 (6H, t), 0.85 (9H, s), 0.89 (9H, s), 0.94 (3H, d, J 6.6), 1.05-2.15 (19H, m), 2.30 (1H, bd), 2.55 (1H, dd), 2.85 (1H, bd), 4.21 (1H, m), 4.52 (1H, m), 4.93 (1H, m), 4.97 (1H, m), 5.50 (1H, d), 5.53 (1H, dd), 5.80 (1H, d, J 11.5), 5.94 (1H, dd), 6.15 (1H, dd), 6.44 (1H, d, J 11.5).

Preparation 22 Compound 114k

The compound was prepared using Procedure 6 in which starting material II was compound 114j. (Eluant: hexane-ether 90:10) 114k; δ (300 MHz) 0.05 (12H, m). 0.4S 3H, s), 0.86 (6H, t), 0.87 (9H, s), 0.88 (9H, s), 0.94 (3H, d, J 6.6), 1.00-2.15 (19H, m), 2.20 (1H, dd), 2.43 (1H, dd), 2.79 (1H, bd), 4.18 (1H, m), 4.36 (1H, m), 4.85 (1H, m), 5.17 (1H, m), 5.50 (1H, d), 5.53 (1H, dd), 5.93 (1H, dd), 6.00 (1H, d), 6.14 (1H, dd), 6.22 (1H, d).

Preparation 23 Compound 117j

The compound was prepared using Procedure 1 in which the starting material was compound 2bj (x=2). (Eluant: hexane-ether 70:30) 117j; δ (300 MHz) 0.05 (12H, m), 0.49 (3H, s), 0.85 (9H, s), 0.89 (9H, s), 0.94 (3H, d, J 6.6), 1.05-2.17 (15H, m), 2.30 (1H, bd), 2.55 (1H, dd), 2.84 (1H, bd), 4.16 (2H, m), 4.21 (1H, m), 4.52 (1H, m), 4.93 (1H, m), 4.97 (1H, m), 5.58 (1H, dd), 5.71 (1H, m), 5.81 (1H, d, J 11.4), 5.96 (1H, dd), 6.20 (1H, dd), 6.44 (1H, d, J 11.4).

Preparation 24 Compound 117k

The compound was prepared using Procedure 6 in which starting material II was compound 117j. (Eluant: hexane-ether 70:30) 117k; δ (300 MHz) 0.05 (12H, m), 0.48 (3H, s), 0.86 (9H, s), 0.87 (9H, s), 0.93 (3H, d), 1.02-2.15 (15H, m), 2.21 (1H, dd), 2.43 (1H, dd), 2.80 (1H, bd), 4.16 (2H, bd), 4.19 (1H, m), 4.36 (1H, m), 4.85 (1H, m), 5.17 (1H, m), 5.57 (1H, dd), 5.70 (1H, m), 5.95 (1H, dd), 6.00 (1H, d), 6.20 (2H, m).

Preparation 25 Compound 119j

The compound was prepared using Procedure 4 in which the alkyl-lithium was n-propyl-lithium and the starting material was 2aj (x=2). 119j; δ (300 MHz) 0.05 (12H, m), 0.55 (3H, s), 0.86 (9H, s), 0.89 (9H, s), 0.89 (6H, t), 1.05 (3H, d, J 6.6), 1.15-2.20 (23H, m), 2.30 (1H, bd), 2.55 (1H, dd), 2.87 (1H, bd), 4.21 (1H, m), 4.52 (1H, m), 4.93 (1H, m), 4.98 (1H, m), 5.50 (1H, dd), 5.54 (1H, d), 5.81 (1H, d, J 11.4), 5.95 (1H, dd), 6.13 (1H, dd), 6.45 (1H, d, J 11.4).

Preparation 26 Compound 119k

The compound was prepared using Procedure 6 in which starting material II was compound 119j. (Eluant: hexane-ether 85:15) 119k; δ (300 MHz) 0.05 (12H, m), 0.54 (3H, s), 0.86 (18H, s), 0.89 (6H, t), 1.04 (3H, d, J 6.6), 1.15-2.15 (23H, m), 2.20 (1H, dd), 2.43 (1H, dd), 2.81 (1H, bd), 4.18 (1H, m), 4.35 (1H, m), 4.85 (1H, m), 5.16 (1H, m), 5.52 (1H, dd), 5.53 (1H, dd), 5.94 (1H, dd), 6.00 (1H, d), 6.12 (1H, dd), 6.22 (1H, d).

Preparation 27 Compound 121k

Compound 121j was prepared by using Procedure 1 in which the starting material was compound 2aj (x=2). The crude 121j was of sufficient purity for use as starting material in Procedure 6 by which method it was transformed into compound 121k. (Eluant: hexane-ether 70:30). 121k; δ (300 MHz) 0.05 (12H, m), 0.54 (3H, s), 0.86 (18H, s), 1.04 (3H, d, J 6.6), 1.12-2.30 (16H, m), 2.44 (1H, dd), 2.82 (1H, bd), 4.15 (2H, m), 4.17 (1H, m), 4.36 (1H, m), 4.85 (1H, m), 5.16 (1H, m), 5.57 (1H, dd), 5.70 (1H, m), 5.97 (1H, dd), 6.00 (1H, d), 6.18 (1H, dd), 6.22 (1H, d).

Preparation 28 Compound 2ak (x=1)

Using the method of Preparation 2 and by starting from 1ak instead of 1aj compound 2ak (x=1) was obtained as an oil. δ (300 MHz) 0.05 (12H, bs), 0.55 (3H, s), 0.87 (18H, s), 1.08 (3H, d), 1.15-2.10 (12H, m), 2.10-2.35 (3H, m), 2.44 (1H, dd), 2.82 (1H, bd), 3.70 (3H, s), 4.18 (1H, m), 4.36 (1H, m), 4.83 (1H, bd), 5.16 (1H, bd), 5.74 (1H, d), 6.00 (1H, d), 6.22 (1H, d), 6.87 (1H, dd).

Preparation 29 Compound 123k

The compound was prepared using Procedure 1 in which the starting material was compound 2ak (x=1). (Eluant: hexane-ether 7 3). 123k; δ (300 MHz) 0.05 (12H, m), 0.54 (3H, s), 0.87 (18H, s), 1.03 (3H, d, J 6.6), 1.12-2.30 (16H, m), 2.44 (1H, dd), 2.82 (1H, bd), 4.06 (2H, m), 4.18 (1H, m), 4.36 (1H, m), 4.85 (1H, m), 5.17 (1H, m), 5.54 (2H, m), 6.00 (1H, d, J 11.2), 6.22 (1H, d, J 11.2).

Preparation 30 Compound 3ak (x=1)

Using the method of Preparation 5 (compound 123k as starting material), compound 3ak (x=1) was prepared and purified by chromatography (Eluant: hexane-ether 4 1). δ (300 MHz) 0.05 (12H, m), 0.57 (3H, s), 0.86 (18H, s), 1.14 (3H, d, J 6.6), 1.10-1.90 (12H, m), 1.98 (1H, bd), 2.21 (1H, dd), 2.43 (2H, m), 2.83 (1H, bd), 4.18 (1H, m), 4.36 (1H, m), 4.85 (1H, m), 5.17 (1H, m), 6.04 (2H, m), 6.22 (1H, d, J 11.3), 6.70 (1H, dd), 9.47 (1H, d, J 7.8).

Preparation 31 Compound 2ak (x=3)

This compound was prepared by using the method of Preparation 6 and by starting from 3ak (x=1) instead of 1aj. The reaction mixture was only kept at 62° C for 2 hours. Compound 2ak (x=3) was isolated by chromatography. (Eluant: hexane-ether 4:1). δ (300 MHz) 0.05 (12H, m), 0.55 (3H, s), 0.87 (18H, s), 1.06 (3H, d, J 6.6), 1.15-2.30 (15H, m), 2.43 (1H, dd), 2.82 (1H, bd), 3.73 (3H, s), 4.18 (1H, m), 4.35 (1H, m), 4.84 (1H, m), 5.16 (1H, m), 5.79 (1H, dd), 5.82 (1H, d), 5.95-6.25 (4H, m), 6.50 (1H, dd), 7.29 (1H, dd).

Preparation 32 Compound 124k

The compound was prepared by following Procedure 4 and by using methyl-lithium and 2ak (x=3) as starting material. (Eluant: hexane-ether 4:1). δ (300 MHz) 0.05 (12H, m), 0.54 (3H, s), 0.86 (18H, s), 1.04 (3H, d, J 6.6), 1.33 (6H, s), 1.15-2.30 (16H, m), 2.44 (1H, dd), 2.82 (1H, bd), 4.18 (1H, m), 4.36 (1H, m), 4.85 (1H, m), 5.16 (1H, m), 5.56 (1H, dd), 5.78 (1H, d), 5.92-6.30 (6H, m).

Preparation 33 Compound 126k

The compound was prepared by following Procedure 4 and by using ethyl-lithium and 2ak (x=3) as starting material. (Eluant: hexane-ether 4:1). δ (300 MHz) 0.05 (12H, m), 0.54 (3H, s), 0.84 (6H, t), 0.87 (18H, s), 1.04 (3H, d, J 6.5), 1.00-2.30 (20H, m), 2.44 (1H, dd), 2.81 (1H, bd), 4.18 (1H, m), 4.36 (1H, m), 4.85 (1H, m), 5.17 (1H, m), 5.56 (1H, dd), 5.59 (1H, d), 6.00 (2H, m), 6.16 (4H, m).

Preparation 34 Compound 128k

This compound was prepared using Procedure 1 in which the starting material was compound 2ak (x=3). δ (300 MHz) 05 (12H, m), 0.54 (3H, s), 0.87 (18H, s), 1.04 (3H, d, J 6.6), 1.12-2.25 (16H, m), 2.43 (1H, dd), 2.82 (1H, bd), 4.18 (3H, m), 4.36 (1H, m), 4.85 (1H, m), 5.16 (1H, m), 5.59 (1H, dd), 5.79 (1H, m), 5.90-6.30 (6H, m).

Preparation 35 Compound 107k

This compound was prepared using Procedure 6 in which starting material II was compound 107j. δ (300 MHz) 0.05 (12H, m), 0.54 (3H, s), 0.87 (18H, s), 1.04 (3H, d), 1.15-2.15 (22H, m), 2.21 (2H, d), 2.40 (1H, m), 2.82 (1H, bd), 4.18 (1H, m), 4.36 (1H, m), 4.85 (1H, m), 5.17 (1H, m), 5.51 (1H, dd), 5.60 (1H, m), 6.00 (3H, m), 6.24 (1H, d).

Procedure 7 Preparation of Compound I from the Corresponding Compound II or V (R=k) (Scheme 4)

A solution of the compound II or V (0.2 g) and tetra-n-butylammonium fluoride trihydrate (0.4 g) in THF (10 ml) was heated at 60° C. under an atmosphere of nitrogen for 50 minutes. After cooling, the reaction solution was partitioned between ethyl acetate (40 ml) and 2% sodium hydrogen carbonate solution (30 ml), and the organic layer was washed with water and brine, dried and concentrated. The residue was purified by chromatography (30 g silica gel, ethyl acetate as eluant) to give I.

The compounds of Examples 1-4 and 6-14 were prepared using procedure 7. The respective starting materials II or V are given in the Examples.

Example 1

20(R)-(5'-Cyclopropyl-5'-hydroxy-penta-1'(E),3'(E)-dien-1'-yl)-1(S), 3(R)-dihydroxy-9,10-secopregna-5(Z), 7(E),10(19)-triene (Isomer A) (Compound 108)

Starting material 102k; δ (300 MHz) 0.20-0.40 (2H, m, 0.53 (3H, s), 0.46-0.65 (2H, m), 1.05 (3H, d, J 6.6), 0.90-2.20 (18H, m), 2.31 (1H, dd), 2.60 (1H, m), 2.83 (1H, m), 3.49 (1H, t), 4.23 (1H, m), 4.43 (1H, m), 5.00 (1H, m), 5.33 (1H, m), 5.57 (1H, dd, J 15 and 8.7), 5.66 (1H, dd, J and 6.5), 5.97 (1H, dd, J 15 and 10.3), 6.01 (1H, d, J 11.2) 6.17 (1H, dd, J 15 and 10.3), 6.38 (1H, d, J 11.2).

Example 2

20(R)-(5'-Cyclopropyl-5'-hydroxypenta-1'(E),3'(E)-dien-1'-yl)-1(S), 3(R)-dihydroxy-9,10-secopregna-5(Z), 7(E),10(19)-triene (Isomer B) (Compound 109)

Starting material: 103k; δ (300 MHz) 0.22-0.40 (2H, m), 0.56 (3H, s), 0.46-0.65 (2H, m), 1.05 (3H, d, J 6.6), 0.90-2.20 (18H, m), 2.31 (1H, dd), 2.60 (1H, m), 2.84 (1H, m), 3.50 (1H, t), 4.23 (1H, m), 4.43 (1H, m), 5.00 (1H, m), 5.33 (1H, m), 5.58 (1H, dd, J 15.1 and 8.6), 5.67 (1H, dd, J 15.2 and 6.3), 5.97 (1H, dd, J 15.1 and 10.3), 6.01 (1H, d, J 11.3) 6.19 (1H, dd, J 15.1 and 10.3), 6.38 (1H, d, J

Example 3 1

1(S),3(R)-Dihydroxy-20(R)-(5'-hydroxy-5'-methyl-hexa-1'(E),3'(E)-dien-1'-yl)-9,10-secopregna-5(Z), 7(E)-10(19)-triene (Compound 110)

Starting material: 104k. Crystallisation from ethyl acetate-hexane gave needles, m.p. 156°-157° C.; λ$_{max}$231 nm (λ=42530) and 264 nm (λ=18040); δ (300 MHz) 0.56 (3H, s), 1.05 (3H, d, J 6,6), 1.34 (6H, s), 1.15-2.20 (17H, m), 2.31 (1H, dd), 2.60 (1H, dd), 2.84 (1H, m), 4.23 (1H, m), 4.43 (1H, m), 5.00 (1H, m), 5.33 (1H, m), 5.56 (1H, dd), 5.71 . (1H, dd, J 15.4), 5.96 (2H, m), 6.16 (1H, dd), 6.38 (1H, d, J 11.2).

Example 4

1(S),3(R)-Dihydroxy-20(R)-(5'-ethyl-5'-hydroxy-hepta-1'(E),3'(E)-dien-1'-yl)-9,10-secopregna-5(Z),7(E), 10(19)-triene (Compound 111)

Starting material: 105k. Crystallisation from methyl format-hexane gave needles, m.p. 123°-125° C.; λ$_{max}$232 nm (λ=43745) and 264 nm (λ=18060); δ (300 MHz) 0.55 (3H, s), 0.85 (6H, t), 1.04 (3H, d, J 6.6), 1.12-2.20 (21H, m), 2.30 (1H, dd), 2.58 (1H, dd), 2.82 (1H, dd), (21H, m), 4.41 (1H, m), 4.99 (1H, m), 5.31 (1H, m), 5.53 (2H, m), 5.95 (1H, dd, J 15 and 10.3), 6.00 (1H, d, J 11.3), 6.14 (1H, dd, J 15 and 10.3), 6.37 (1H, d, J 11.3).

Example 5 1

1(S),3(R)-Dihydroxy-20(R)-(6'-hydroxy-hexa-1'(E),3-'(E)-dien-1'-yl)-9,10-secopregna-5(Z),7(E),10(19)-triene (Compound 112)

A solution of MC 903 [M. J. Calverley, Tetrahedron 43, (1987)](0.45 g) in a mixture of alcohol-free chloroform (20 ml) and trifluoroacetic anhydride (9 ml) was kept at room temperature for 50 minutes. The reaction mixture was then slowly added to an ice-cold stirred solution of potassium hydroxide (19.8 g) in methanol (150 ml). After stirring for 10 minutes and concentration in vacuo, the residue was partitioned between methylene chloride and water. The organic layer was dried and concentrated. Purification by chromatography (silica gel, hexane-ethyl acetate 1:3 as eluant) gave the title compound which crystallized from ethyl acetate, m.p.: 132°-35° C; λ$_{max}$=232 nm (λ=40980) and 264 nm (λ=17494); δ(300 MHz) 0.56 (3H, s), 1.04 (3H, d, J 6.6), 1.15-2.25 (17H, m), 2.32 (3H, m), 2.60 (1H, dd), 2.82 (1H, dd), 3.66 (2H, m), 4.22 (1H, m), 4.43 (1H, m), 4.99 (1H, s), 5.32 (1H, s), 5.50 (2H, m), 6.00 (3H, m), 6.37 (1H, d, J 11.2):

Example 6

1(S),3(R)-Dihydroxy-20(R)-(6'-hydroxy-6'-methyl-hepta-1'(E),3'(E)-dien-1'-yl)-9,10-secopregna-5(Z), 7(E)-10(19)-triene (Compound 133)

Starting material: 107k; Crystallization from methyl formate-hexane, m.p. 147°–148° C.; $\lambda_{max}$233 nm ($\lambda$=43322) and 264 nm ($\lambda$=17916); $\delta$(300 MHz) 0.56 (3H, s), 1.05 (3H, d), 1.22 (6H, s), 1.20–2.20 (17H, m), 2.23 (2H, d), 2.31 (1H, dd), 2.60 (1H, dd), 2.83 (1H, bd), 4.23 (1H, m), 4.43 (1H, m), 5.00 (1H, m), 5.32 (1H, m), 5.50 (1H, dd), 5.60 (1H, m), 6.01 (3H, m), 6.38 (1H, d).

Example 7

1(S),3(R)-Dihydroxy-20(R)-(7'-hydr-oxy-hepta-1'(E),3'(E),5'(E)-trien-1'-yl)-9,10-secopregna-5(Z),7(E),-10(19)-triene (Compound 129)

Starting material: 128k; $\delta$(300 MHz) 0.59 (3H, s), 1.Q6 (3H, d, J 6.6), 1.89 (2H, t), 1.15–2.21 (15H, m), 2.25 (1H, dd), 2.52 (1H, dd), 2.87 (1H, bd), 4.09 (2H, bd), 4.12 (1H, m), 4.35 (1H, m), 4.89 (1H, m), 5.28 (1H, m), 5.56 (1H, dd), 5.75 (1H, m), 5.95–6.36 (6H, m).

Example 8

1(S),3(R)-Dihydroxy-20(S)-(5'-hydroxy-5'-methyl-hexa-1'(E),3'(E)-dien-1'-yl)-9,10-secopregna-5(Z), 7(E),10(19)-triene (Compound 115)

Starting material: 113k. The compound crystallized from ethyl acetate-hexane, m.p. 98°–102° C.; $\lambda_{max}$232 nm ($\epsilon$=and 265 nm ($\epsilon$=17418); $\delta$(300 MHz) 0.50 (3H, s), 0.94 (3H, d, J 6.6), 1.35 (6H, s), 1.05–2.15 (17H, m), 2.31 (1H, dd), 2.57 (1H, bd), 2.82 (1H, bd), 4.22 (1H, m), 4.43 (1H, m), 5.00 (1H, m), 5.33 (1H, m), 5.56 (1H, dd), 5.69 (1H, d), 5.92 (1H, dd), 6.01 (1H, d, J 11.3), 6.16 (1H, dd), 6.37 (1H, d, J 11.3).

Example 9

1(S),3(R)-Dihydroxy-20(S)-(5'-ethyl-5'-hydroxy-hepta-1'(E),3'(E)-dien-1'-yl)-9,10-secopregna-5(Z),7(E), 10(19)-triene (Compound 116)

Starting material: 114k; $\lambda_{max}$233 and 264 nm; $\delta$(300 MHz) 0.51 (3H, s), 0.87 (6H, t), 0.95 (3H, d, J 6.7), 1.02–2.15 (21H, m), 2.31 (1H, dd), 2.60 (1H, bd), 2.81 (1H, bd), 4.23 (1H, m), 4.43 (1H, m), 5.00 (1H, m), 5.33 (1H, m), 5.51 (1H, d), 5.53 (1H, dd), 5.95 (1H, dd), 6.01 (1H, d), 6.16 (1H, dd), 6.38 (1H, d, J 11.2).

Example 10

1(S),3(R)-Dihydroxy-20(S)-(5'-hydroxy-penta-1'(E),3'(E)-dien-1'-yl)-9,10-secopregna-5(Z),7(E), 10(19)-triene (Compound 118)

Starting material: 117k; $\delta$(300 MHz) 0.50 (3H, s), 0.94 (3H, d, J 6.6), 1.02–2.20 (17H, m), 2.31 (1H, dd), 2.59 (1H, dd), 2.81 (1H, bd), 4.17 (2H, bd), 4.23 (1H, m), 4.42 (1H, m), 5.00 (1H, m), 5.33 (1H, m), 5.58 (1H, dd), 5.72 (1H, m), 5.96 (1H, dd), 6.01 (1H, d, J 11.3), 6.21 (1H, dd), 6.37 (1H, d, J 11.3).

Example 11

1(S), 3(R)-Dihydroxy-20(R)-(5'-hydroxy-5,-n-propyl-octa-1'(E),3'(E)-dien-1'-yl)-9,10-secopregna-5(Z), 7(E),10(19)-triene (Compound 120)

Starting material: 119k; $\delta$(300 MHz) 0.55 (3H, s), 0.89 (6H, t), 1.04 (3H, d, J 6.6), 1.15–2.18 (25H, m), 2.30 (1H, dd), 2.59 (1H, dd), 2.82 (1H, bd), 4.21 (1H, m), 4.41 (1H, m), 4.98 (1H, m), 5.31 (1H, m), 5.52 (1H, dd), 5.54 (1H, d), 5.93 (1H, dd), 6.00 (1H, d) 6.12 (1H, dd), 6.36 (1H, d, J 11.2).

Example 12

1(S),3(R)-Dihydroxy-20(R)-(5'-hydroxy-penta-1'(E),3'(E)-dien-1''-yl-9,10-secopregna-5(Z),7(E), 10(19)-triene (Compound 122)

Starting material: 121k. Crystals from methyl formate; m.p.: 154°–155° C.; $\lambda_{max}$231 nm ($\epsilon$=41228) and 264 nm ($\epsilon$=17876); $\delta$(300 MHz) 0.58 (3H, s), 1.05 (3H, d, J 6.6), 1.15–1.80 (12H, m), 1.89 (2H, t), 2.01 (2H, m), 2.14 (1H, m), 2.26 (1H, dd), 2.52 (1H, dd), 2.87 (1H, bd), 4.06 (2H, m), 4.12 (1H, m), 4.35 (1H, t), 4.89 (1H, m), 5.28 (1H, m), 5.53 (1H, dd), 5.67 (1H, d), 5.98 (1H, dd), 6.08 (1H, d, J 11.2), 6.16 (1H, dd), 6.32 (1H, d, J 11.2).

Example 13

1(S),3(R)-Dihydroxy-20(R)-(7'-hydroxy-7'-methyl-octa-1'(E),3'(E)-5'(E)-trien-1'-yl)-9,10-secopregna-5(Z),7(E),10(19)-triene (Compound 125

Starting material: 124k. Compound 125 was crystallized from methyl formate; $\lambda_{max}$259 nm (E =53692), nm ($\epsilon$=67103), and 279 nm ($\epsilon$=53256); $\delta$(300 MHz) 0.56 (3H, s), 1.05 (3H, d, J 6.6), 1.34 (6H, s), 1.15–2.20 (17H, m), 2.31 (1H, dd), 2.60 (1H, bd), 2.83 (1H, bd), 4.22 (1H, m), 4.42 (1H, m), 4.99 (1H, m), 5.32 (1H, m), 5.57 (1H, dd), 5.79 (1H, d), 5.90–6.30 (5H, m), 6.38 (1H, d, J

Example 14

1(S),3(R)-Dihydroxy-20(R)-(7'-hydroxy-7'-ethyl-nona-1'(E),3'(E)-5'(E)-trien-1'-yl)-9,10-secopregna-5(Z),7(E),10(19)-triene (Compound 127

Starting material 126k. Crystals from methyl formate-hexane; m.p.: 115°–118° C. $\lambda_{max}$260 nm ($\epsilon$=58040), 270 nm ($\epsilon$=72111), and 281 nm ($\epsilon$=56714); $\delta$(300 MHz) 0.56 (3H, s), 0.85 (6H, t), 1.05 (3H, d, J 6.6), 1.15–2.20 (21H, m), 2.31 (1H, dd), 2.60 (1H, dd), 2.83 (1H, bd), 4.22 (1H, m), 4.42 (1H, m), 5.00 (1H, m), 5.32 (1H, m), 5.59 (1H, dd), 5.61 (1H, d), 6.00 (2H, m), 6.10–6.30 (3H, m), 6.37 (1H, d, J 11.3).

Example 15

20(S)-(5'-Cyclopropyl-5'-hydroxy-penta-1'(E),3'(E)-dien-1'-yl)-1(S), 3(R)-dihydroxy-9,10-secopregna-5(Z), 7(E),10(19)-triene (Compounds 131 and 132)

These two isomeric compounds are prepared by using the procedures described in Preparations 8, 9, 14, 15 and Examples 1 and 2 and by substituting 3b (x=1) (described in British patent application No. 8914963.7) for 3aj (x=1) in Preparation 8.

Example 16

1S),3(R)-Dihydroxy-20(S)-(6'-hydroxy-hexa-1'(E),3'(E)-dien-1'-yl)-9,10-secopregna-5(Z),7(E),10(19)-triene (Compound 130)

This compound was prepared by following the procedure described in Example 5 and by using 20(S)-(3'-cyclopropyl-3'-hydroxyprop-1'(E)-enyl)-1(S),3(R)-dihydroxy-9,10-secopregna-5(Z),7(E),10(19)-triene - isomer A or isomer B or mixtures thereof - (described in British patent application No. 8914963.7) as starting material instead of MC 903.

$\delta$(300 MHz) 0.50 (3H, s), 0.93 (3H, d), 1.05–2.10 (17H, m), 2.30 (1H, m), 2.34 (2H, q), 2.58 (1H, dd), 2.81 (1H, bd), 3.67 (2H, t), 4.22 (1H, m), 4.42 (1H, m), 4.99 (1H, bs), 5.32 (1H, bs), 5.45–5.60 (2H, m), 5.85–6.15 (3H, m), 6.37 (1H, d).

Example 17

1(S),3(R)-Dihydroxy-20(S)-(6'-hydroxy-6'-methyl-hepta-1'(E),3'(E)-dien-1'-yl)-9,10-secopregna-5(Z), 7(E),10(19)-triene (Compound 134)

This compound is prepared by using the procedure described in Preparations 13 and 35 and Procedure 7 and by substituting 3bj (x=1) (described in British patent application No. 8914963.7) for 3aj (x=1) in Preparation 13.

Example 18

1(S),3(R)-Dihydroxy-20(S)-(6'-ethyl-6'-hydroxy-octa-1'(E),3'(E)-dien-1'-yl)-9,10-secopregna-5(Z), 7(E),10(19)-triene (Compound 135)

This compound is prepared by using the procedure described in Example 17 but substituting compound 12 for compound 11 in Preparation 13.

Example 19

1(S),3(R)-Dihydroxy-20(R)-(6'-ethyl-6'-hydroxy-octa-1'(E),3'(E)-dien-1'-yl)-9,10-secopregna-5(Z), 7(E),10(19)-triene (Compound 136)

This compound is prepared by using the procedure described in Preparations 13 and 35 and Procedure 7 but substituting compound 12 for compound 11 in Preparation 13; δ(300 MHz) 0.56 (3H, s), 0.88 (6H, t), 1.04 (3H, d), 7 30 1.48 (4H, q), 1.15–2.17 (17H, m), 2.20 (2H, d), 2.32 (1H, dd), 2.60 (1H, dd), 2.83 (1H, dd), 4.23 (1H, m), 4.43 (1H, m), 5.00 (1H, m), 5.32 (1H, m), 5.52 (2H, m), 6.00 (3H, m), 6.38 (1H, d).

Example 20

1(S),3(R)-Dihydroxy-20-(5',6'-dimethyl-6'-hydroxy-hepta-1'(E),3 (E)-dien-1'-yl)-9,10-secopregna-5(Z), 7(E),10(19)-triene (Compounds 137–140)

The four diastereoisomers of the title compound are prepared separately using the methods of Procedures 5, 6 and 7 and the appropriate starting materials 3aj (x=1) or bj (x=1) and 17 or 18.

Example 21

Dermatological Cream Containing Compound 111

In 1 g almond oil was dissolved 0.1 mg 111. To this solution was added 40 g of mineral oil and 20 g of self-emulsifying beeswax. The mixture was heated to liquify. After the addition of 40 ml hot water, the mixture was mixed well. The resulting cream contains approximately 1 μg of 111 per gram of cream.

Example 22

Capsules containing Compound 111

111 was suspended in arachis oil to a final concentration of 5 μg 111/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 μl of the 111 in oil suspension, such that each capsule contained 0.5 μg 111.

What we claim is:

1. A compound of the formula I

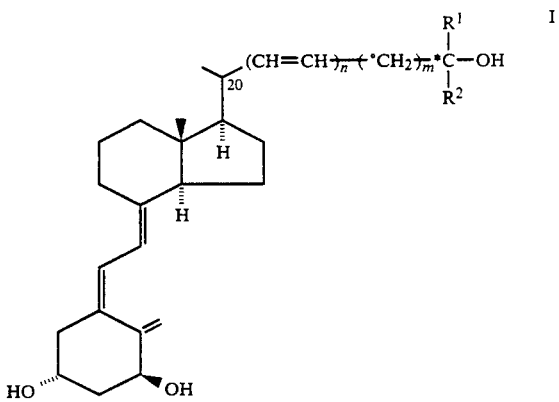

in which formula, n is 2 or 3, m is 0 or an integer from 1 –4; $R^1$ and $R^2$ (which may be the same or different) stand for hydrogen or $C_1$–$C_8$, hydrocarbyl indicating the residue after removal of a hydrogen atom from a straight, branched or cyclic saturated or unsaturated hydrocarbon, or taken together with the carbon bearing the hydroxyl group (starred in formula I), $R^1$ and $R^2$ can form a saturated or unsaturated $C_3$–$C_8$ carbocyclic ring; in addition, $R^1$ and/or $R^2$ and/or one of the m carbons designated by the ". " may be optionally substituted with one or more chlorine or fluorine atom(s); and finally one of the carbons designated "." may optionally be substituted by one or two $C_1$–$C_2$ alkyl group(s); and derivatives of the compounds pounds of formula I in which one or more hydroxy have been transformed into -O-acyl or -O-glycosyl or phosphate ester groups; such masked groups being hydrolyzable in vivo; and other prodrugs thereof.

2. A diastereoisomer of a compound according to claim 1, in pure form; or a mixture of diastereoisomers of a compound according to claim 1.

3. A compound according to claim 1 selected from the groups consisting of the 20(R) and 20(S) isomers of:
1(S),3(R)-Dihydroxy-20-(5'-hydroxy-5'-methyl-hexa-1'(E),3'(E)-dien-1'-yl)-9,10-secopregna-5(Z),7(E),-10(19)-triene;
1(S),3(R)-Dihydroxy-20-(5'-ethyl-5'hydroxy-hepta-1'(E),3'(E)-dien-1'-yl)-9,10-secopregna-5(Z),7(E),-10(19)-triene;
1(S),3(R)-Dihydroxy-20-(6'-hydroxy-hexa-1'(E),-3'(E)-dien-1'-yl)-9,10-secopregna-5(Z),7(E),-10(19)-triene;
1(S),3(R)-Dihydroxy-20-(5'-cyclopropyl-5'-hydroxy-penta-1'(E),3'(E)-dien-1'-yl)-9,10-secopregna-5(Z),-7(E),10(19)-triene (5'(R) and 5'(S) isomers);
1(S),3(R)-Dihydroxy-20-(6'-hydroxy-6'-methyl-hepta-1'(E),3'(E)-dien-1'-yl)-9,10-secopregna-5(Z),7(E),-10(19)-triene;

4. A pharmaceutical composition containing an effective amount of one or more of the compounds of claim 1, together with pharmaceutically acceptable, non-toxic carriers and/or auxiliary agents.

5. A pharmaceutical composition according to claim 4 for topical use containing from 0.1–100 μg/g of a compound of formula I.

6. A pharmaceutical composition according to claim 4 in dosage unit form.

7. A dosage unit according to claim 6 containing from 0.01–100 μg for oral and parenteral formulations of a compound of formula I.

* * * * *

UNITED STATES PATENT AND TRADEMARK OFFICE
CERTIFICATE OF CORRECTION

PATENT NO. : 5,190,935
DATED : March 2, 1994
INVENTOR(S) : BINDERUP et al.

It is certified that error appears in the above-indentified patent and that said Letters Patent is hereby corrected as shown below:

Column 7, line 44, change "$Z-(CH_2)_m-C(R^1)(R^2)--OR^3$" to --$Z-(°CH_2)_m-C(R^1)(R^2)-OR^3$--;

Column 7, line 52, change "$Z=ph_3P^{30}-CH_2-$ or" to --$Z=ph_3P^+-CH_2-$ or ---;

Column 8, line 3 change "fragements" to --fragments--;

Column 8, line 4, change "appropraite" to --appropriate--;

Column 8, line 56, Table 3, change "m" to --$\overset{+}{\underset{m}{+}}$--;

Column 8, line 67, preceding "Unsubstituted" insert --$\overset{+}{\underset{+}{\phantom{+}}}$--;

UNITED STATES PATENT AND TRADEMARK OFFICE
CERTIFICATE OF CORRECTION

PATENT NO. : 5,190,935
DATED : March 2, 1994
INVENTOR(S) : BINDERUP et al.

It is certified that error appears in the above-indentified patent and that said Letters Patent is hereby corrected as shown below:

Column 9-10, Table 4, in the headings, change "m" to $--\genfrac{}{}{0pt}{}{+}{m}--$;

Column 9, following Table 4, preceding "Note as for Table 3" insert $--\genfrac{}{}{0pt}{}{+}{+}--$;

Column 9, Table 5, in the heading, change "m" to $--\genfrac{}{}{0pt}{}{+}{m}--$;

Column 11, line 11, change ")m -- CH($R^1$)($R^2$)" to --)m -CH($R^1$)($R^2$)--;

Column 13, line 40, change "TM broad" to -- =broad--;

UNITED STATES PATENT AND TRADEMARK OFFICE
CERTIFICATE OF CORRECTION

PATENT NO. : 5,190,935
DATED : March 2, 1994
INVENTOR(S) : BINDERUP et al.

It is certified that error appears in the above-indentified patent and that said Letters Patent is hereby corrected as shown below:

Column 14, line 12, change "90" to --9.0--;

Column 14, line 36, change "Preparation 4:1" to --Preparation 4:--;

Column 14, line 49, change "4.g8" to --4.98--;

Column 15, line 23, change "bonyl)TM2"- to --bonyl)-2- --;

Column 15, line 29, change "91" to --9.1--;

Column 15, line 66, change "$\lambda$max 2792 nm" to --$\lambda$max 279.2 nm--;

UNITED STATES PATENT AND TRADEMARK OFFICE
CERTIFICATE OF CORRECTION

PATENT NO. : 5,190,935
DATED : March 2, 1994
INVENTOR(S) : BINDERUP et al.

It is certified that error appears in the above-indentified patent and that said Letters Patent is hereby corrected as shown below:

Column 18, line 53, change "$\delta\max = 268nm$" to --$\lambda\max = 268nm$--;

Column 18, line 65 change "MeOH; $\delta\max$ 232 nm;" to --MeOH; $\lambda\max$ 232 nm --;

Column 19, line 31, change "0.453H,s)" to --0.483H,$^s$--;

Column 20, line 39, change "73" to --7:3--;

Column 20, line 50, change "ether 41)" to --ether 4:1)--;

Column 20, line 59, delete "30"; Column 14, line 12, change "90" to --9.0--;

UNITED STATES PATENT AND TRADEMARK OFFICE
CERTIFICATE OF CORRECTION

PATENT NO. : 5,190,935
DATED : March 2, 1994
INVENTOR(S) : BINDERUP et al.

It is certified that error appears in the above-indentified patent and that said Letters Patent is hereby corrected as shown below:

Column 22, line 15, change "(1H,d,J" to --(1 H, d, J 11.3).--;

Column 22, line 17, change "Example 3 1" to --Example 3--;

Column 22, line 23, change "$\lambda$max 231 nm ($\lambda$ = 42530) and 264 nm ($\lambda$ = 18040); $\delta$ (300" to --$\lambda$max 231 nm ($\epsilon$ = 42530) and 264 nm ($\epsilon$ = 18040); $\delta$ (300--;

Column 22, line 38, change "nm ($\lambda$ = 43745) and 264 nm ($\lambda$ = 18060);" to --nm ($\epsilon$ = 43745) and 264 nm ($\epsilon$ = 18060);--;

Column 22, line 45, change "Example 51" to --Example 5--;

Column 22, line 63, change "($\lambda$ = 40980)" to --($\epsilon$ = 40980)--;

UNITED STATES PATENT AND TRADEMARK OFFICE
CERTIFICATE OF CORRECTION

PATENT NO. : 5,190,935
DATED : March 2, 1994
INVENTOR(S) : BINDERUP et al.

It is certified that error appears in the above-indentified patent and that said Letters Patent is hereby corrected as shown below:

Column 22, line 64, change "($\lambda$ = 17494)" to --($\epsilon$ = 17494)--;

Column 23, line 1, change "Example 61" to --Example 6--;

Column 23, line 8, chanage " ($\lambda$ = 17916)" to --($\epsilon$ = 17916)--;

Column 23, line 15, change "(7'-hydr-oxy-hepta-1'" to --(7'-hydroxy-hepta-1'--;

Column 23, line 18, change "1.Q6" to --1.06--;

Column 23, line 63, change "(5'-hydroxy-5,-n-propyl-octa-" to --(5'-hydroxy-5'-n-propyl-octa--;

UNITED STATES PATENT AND TRADEMARK OFFICE
CERTIFICATE OF CORRECTION

PATENT NO. : 5,190,935
DATED : March 2, 1994
INVENTOR(S) : BINDERUP et al.

It is certified that error appears in the above-indentified patent and that said Letters Patent is hereby corrected as shown below:

Column 24, line 7, change "(E)-dien-1"-yl-9," to --(E)-dien-1'-yl-9--;

Column 24, line 24, change "(E=53692)," to --($\epsilon$ = 53692),--;

Column 24, line 29, change "6.38 (1H,d,J" to --6.38 (1H, d, J 11.2).--; and

Column 25, line 33, change "d), 730 1.48 (4H, q)," to --d), 1.48 (4H,q),--.

Signed and Sealed this

Eighteenth Day of October, 1994

BRUCE LEHMAN

Attest:

Attesting Officer

Commissioner of Patents and Trademarks